United States Patent [19]

Law et al.

[11] Patent Number: 4,742,829

[45] Date of Patent: May 10, 1988

[54] INTRACAVITARY ULTRASOUND AND BIOPSY PROBE FOR TRANSVAGINAL IMAGING

[75] Inventors: Wing Law, Gold River; Wayne Barbour, Rancho Cordova; Axel F. Brisken, Shingle Springs, all of Calif.

[73] Assignee: General Electric Company, Milwaukee, Wis.

[21] Appl. No.: 895,343

[22] Filed: Aug. 11, 1986

[51] Int. Cl.⁴ .............................................. A61B 10/00
[52] U.S. Cl. ..................................... 128/660; 128/754
[58] Field of Search .............................. 128/660–663, 128/24 A, 4, 6, 748–760, 763, 768

[56] References Cited

U.S. PATENT DOCUMENTS

| | | | |
|---|---|---|---|
| 3,173,414 | 3/1965 | Guillant | 128/752 |
| 3,556,079 | 1/1971 | Omizo | 128/661 |
| 3,595,217 | 7/1971 | Renneman | 128/753 X |
| 4,194,513 | 3/1980 | Rhine et al. | 128/750 |
| 4,249,539 | 2/1981 | Vilkomeison et al. | 128/754 X |
| 4,378,810 | 4/1983 | Ishizaki et al. | 128/754 |
| 4,489,727 | 12/1984 | Matsuo et al. | 128/660 |
| 4,576,175 | 3/1986 | Epstein | 128/660 |
| 4,582,061 | 4/1986 | Fry | 128/660 X |
| 4,582,067 | 4/1986 | Silverstein et al. | 128/663 |
| 4,605,009 | 8/1986 | Pourcelot et al. | 128/660 |
| 4,608,989 | 9/1986 | Drue | 128/660 |

*Primary Examiner*—Francis J. Jaworski
*Attorney, Agent, or Firm*—Flehr, Hohbach, Test, Albritton & Herbert

[57] ABSTRACT

An ultrasound probe for positioning in the vaginal cavity includes a phased array of transducer elements at one end thereof oriented at an acute angle with respect to the central axis of the probe whereby the imaging field of view is provided by rotating the probe. A biopsy needle assembly snaps onto slots on the probe with a fork and socket fit. A handle on the probe is offset from the central axis of the probe thereby freeing the space around the entrance to the needle guide and facilitating the manipulation by hand of a needle in the guide.

5 Claims, 2 Drawing Sheets

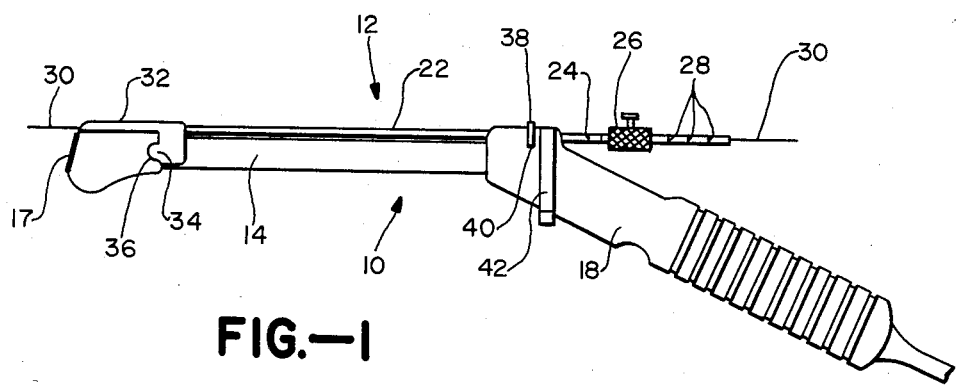
FIG.—1
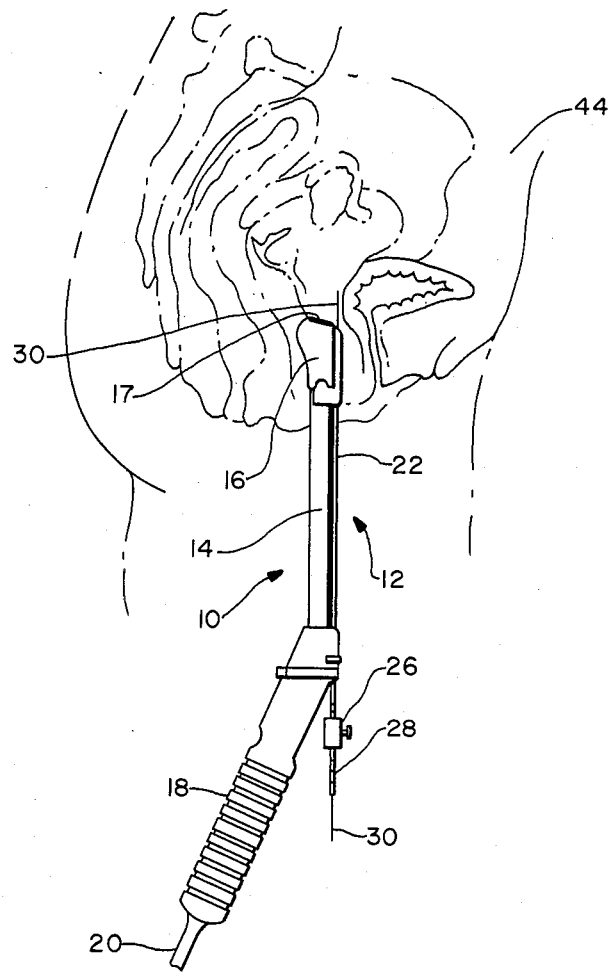
FIG.—2

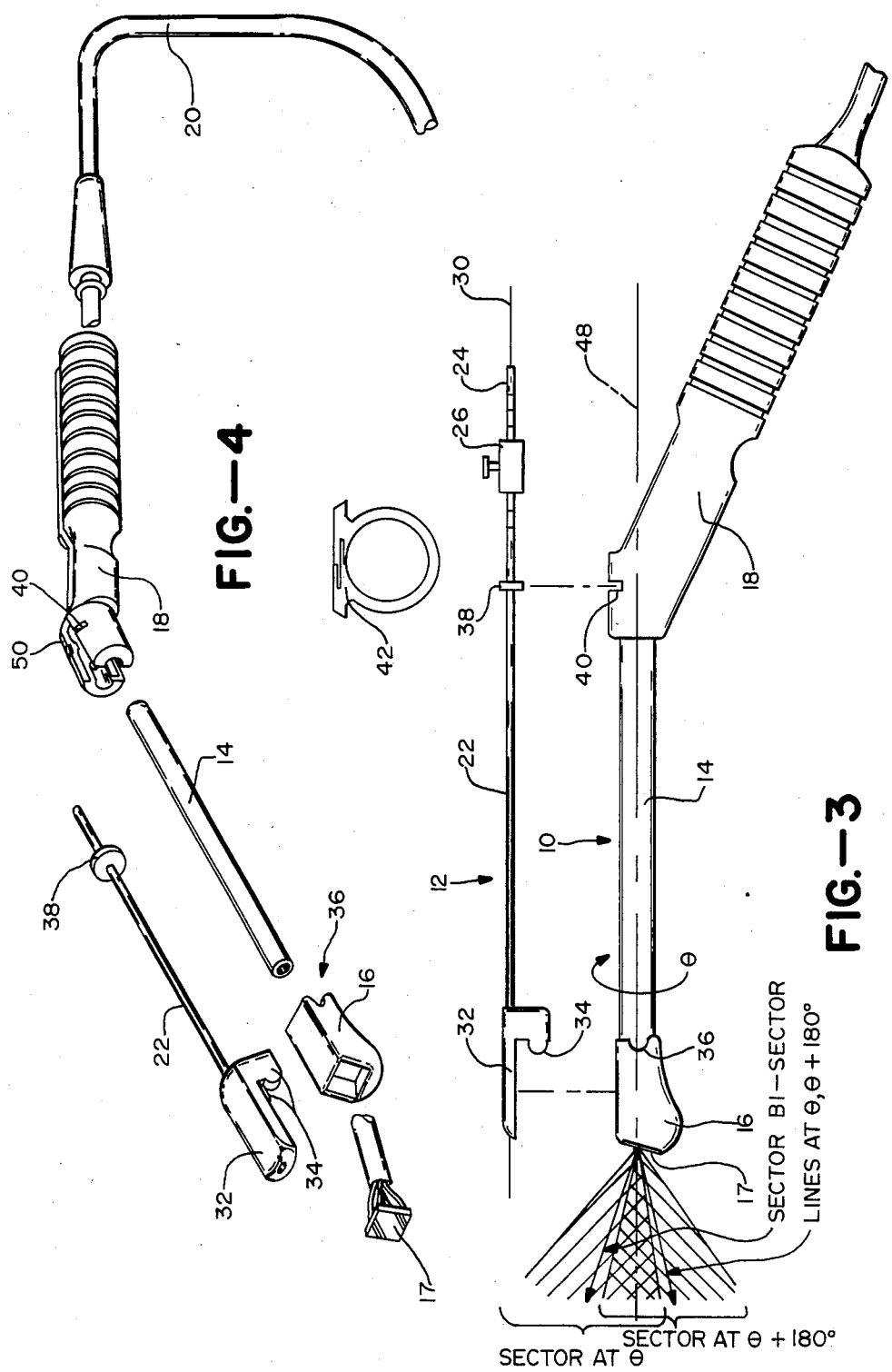

INTRACAVITARY ULTRASOUND AND BIOPSY PROBE FOR TRANSVAGINAL IMAGING

BACKGROUND OF THE INVENTION

This invention relates generally to ultrasound imaging systems, and more particularly the invention relates to an intracavity probe for trans-vaginal imaging and including an integrated biopsy adapter.

Ultrasound imaging has become an important tool in obstetrics for monitoring the fetus during early months of pregnancy and for guiding needles for the extraction of ovum from the ovary for in vitro fertilization and for chorionic villus sampling. Originally, the procedure included abdominal imaging and puncture. However, this procedure can be painful and risks puncturing the bowel loop. Further, large distance of the ovary, uterus, and the fetus to the probe in trans-abdominal scans limits image resolution. More recently, trans-vaginal imaging using an intracavitary probe has been developed and offers many advantages over trans-abdominal imaging. Importantly, the proximity of the organs to the probe during early pregnancy are only one to five centimeters from the vagina as compared to five to fifteen centimeters for trans-abdominal scans. Since the resolution of an image is approximately proportional to distance, the trans-vaginal image will be of superior resolution. Additionally, since less intervening tissue is between the probe and target the signal-to-noise ratio is greatly improved, especially in obese patients. Due to the short propagation distance, high frequency imaging and accurate tissue characterization using high frequency (e.g. 7–10 MHz) imaging is possible in trans-vaginal scans. Further, in trans-abdominal scanning a full bladder is required to serve as a "window" for imaging. This causes discomfort to the patient and may sometimes delay or compromise a scan due to a non-full bladder. Finally, ultrasonic needle guidance may be accomplished trans-vaginally for the extraction of ovum from the ovary and precise biopsy operations can be performed more safely and less painfully.

One intracavity probe now commercially available employs a mechanical section scanning element mounted inside an elongated housing for rotation therein. The scanning head is relatively large and the image quality is marginal. The probe does accommodate a biopsy needle. Another known probe includes an oscillating transducer in an elongated housing. To alter the image scan direction the elongated housing must be axially tilted in the vaginal cavity, causing discomfort and pain to the patient. The probe does not function as a biopsy needle guide.

SUMMARY OF THE INVENTION

The present invention is directed to an improved intracavitary ultrasound and biopsy probe that provides improved images and is more easily operated and manipulated during use. The overall shape, scanned geometry, and needle guide are designed for optimal application.

Briefly, the intracavity ultrasound probe includes an elongated body having a central axis, a transducer assembly fastened to one end of the body with the transducer assembly having a generally planar surface oriented at an acute angle to the axis, and a handle extending from the opposing end of the body. A wide field of view is accommodated with the probe by rotating the elongated body in the vaginal cavity without requiring a tilting thereof. In a preferred embodiment the transducer assembly comprises a phased array of transducer elements which improve the focusing and imaging of organs and the guidance of the biopsy needle.

The biopsy needle assembly is detachably mounted to the probe for obtaining tissue and fluid samples. The assembly includes a needle and an elongated guide for receiving and guiding the needle, the elongated guide having projecting members at one end thereof which engage slots in the transducer assembly housing in a fork and socket fit.

In accordance with one feature of the invention the handle of the probe has an offset angle from the shaft which frees the space around the entrance of the needle guide. The obstruction-free space facilitates the manipulation of the needle by hand and accommodates the attachment of an automatic needle injector. The needle tip may be retracted inside the needle guide between biopsies to avoid accidentally puncturing a patient.

The probe is designed to accept disposable sterile sheaths or condoms for the protection of the patient from bacterial infection during a biopsy and to avoid the transmission of disease between patients.

The invention and objects and features thereof will be more readily apparent from the following detailed description and appended claims when taken with the drawing.

BRIEF DESCRIPTION OF THE DRAWINGS

FIG. 1 is a side elevation view of a probe in accordance with one embodiment of the invention.

FIG. 2 is an illustrative view of use of the probe of FIG. 1 in trans-vaginal examination.

FIG. 3 is a side elevation view of the probe with the biopsy needle assembly removed therefrom.

FIG. 4 is an exploded perspective view of the probe and biopsy needle assembly.

DETAILED DESCRIPTION OF ILLUSTRATIVE EMBODIMENTS

Referring now to the drawings, FIG. 1 is a side elevation view of an intracavity ultrasound probe shown generally at 10 with a biopsy needle assembly shown generally at 12 mounted thereon in accordance with one embodiment of the invention. The probe 10 includes an elongated body or shaft 14 with a transducer assembly including a boot or housing 16 and a transducer array 17 mounted on one end thereof. At the opposing end of shaft 14 is a handle 18. A cord 20 includes electrical wires extending through the handle 18, shaft 14 and housing 16 to the transducer array 17 for communicating electrical signals between the transducer array and the ultrasound processing and imaging system.

The biopsy needle assembly 12 includes a guide 22 for a biopsy needle 24. A needle stop 26 is provided on the needle 24 for limiting penetration thereof. Distance marks 28 on needle 24 facilitate the setting of penetration depth. The biopsy needle 24 is hollow, and provided within the needle 24 is an inner needle 30 that can be extracted for allowing tissue samples to enter the biopsy needle 24.

FIG. 2 illustrates operation of the intracavity probe as inserted into the vaginal cavity of a patient 44 for imaging the ovary, uterus, and fetus during early pregnancy, for example. As noted above, these organs are only one to five centimeters from the transducer array 17 when placed in the vaginal cavity, as compared to 5 to 15 centimeters in the case of trans-abdominal scans, thereby facilitating an image of superior resolution.

FIG. 3 is a side view in elevation with the biopsy needle assembly 12 removed from the probe assembly 10 and further illustrating features thereof. Mounted to the forward end of needle guide 22 is a mount 32 having projections 34 that engage slots 36 in the housing 16. Accordingly, the biopsy guide can be snapped into the slots on the probe with the guide locked into place with a fork and socket behind the probe head. A disc 38 on the guide 22 mates with a slot 40 in the handle 18, and a ring clamp 42 maintains the biopsy assembly 12 firmly in place on the probe assembly 10. It will be noted that the probe has a shaft smaller in diameter than the head for a wide angle of manipulation.

As noted in FIG. 3, the shaft 14 has a central axis 48, and the handle 18 of the probe has an offset angle from the axis, thereby freeing the space around the entrance of the needle guide. The obstacle free space facilitates the manipulation of the needle by hand and for the optional attachment of an automatic needle injector. The needle stop 26 clamps onto the needle and will stop the forward motion of the needle at a preset distance of penetration. This feature allows the use of substantial force in the act of puncture without fear of over-inserting the needle.

In accordance with another feature of the invention the generally planar surface of the transducer array 17 is at an acute angle (e.g. 15°) with the axis 48. Therefore, after the probe is inserted into the vaginal cavity the probe can be rotated about the axis 48 to increase the field of view of the ultrasound image. This mode of operation is less discomforting to the patient than is required with the known prior art probes.

FIG. 4 is an exploded perspective view of the probe and needle assembly further illustrating the components thereof. The hollow shaft 14, transducer assembly housing 16, and handle 18 are preferably injection molded components with the shaft 14 inserted and bonded in the housing 16 and handle 18. It will be noted that handle 18 has a slot 50 on its upper surface for receiving the biopsy guide 22. The transducer array 17 can be a conventional phased array of transducer elements as employed in the General Electric Company RT 3000 phased array echocardiography system, for example.

The intra-cavity ultrasound probe and biopsy assembly in accordance with the invention provides an improved image with a wide angle of view and can be employed with minimum discomfort to the patient. The probe is designed to accept disposable sheaths, and the sterile biopsy guide can be readily snapped onto the slots of the sheath covered probe.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. An intravaginal ultrasound probe and biopsy needle assembly, said probe comprising:
   a rigid elongated body having a central axis,
   a transducer assembly having an end boot portion, said end boot portion being enlarged relative to said elongated body and fastened to one end of said body, and a transducer scanning array supported by said end boot portion
   a handle extending from an opposing end of said body, conductive means extending through said body and electrically contacting said transducer assembly, and
   said biopsy needle assembly including a needle and an elongated guide means for receiving and guiding said needle; said guide means having an axis in parallel alignment with said axis of said elongated body and detachably mounted on said probe said needle assembly being for obtaining tissue and fluid samples,
   said transducer assembly having a generally planar emission surface oriented at an acute angle with respect to said axis of said elongated body and said axis of said guide means.

2. The intravaginal ultrasound probe and biopsy needle assembly as defined by claim 1, wherein said elongated guide means has projecting members at one end thereof, said end boot portion including slots for receiving said projecting members in a fork and socket fit, whereby said biopsy needle assembly is detachably mounted to said probe.

3. The intravaginal ultrasound probe and biopsy needle assembly as defined by claim 2 and further including a ring clamp means for clamping the opposing end of said guide means to said handle.

4. The intravaginal ultrasound probe and biopsy needle assembly as defined by claim 1 wherein said handle has an offset angle from said axis of said elongated body.

5. The intravaginal ultrasound probe and biopsy needle assembly as defined by claim 1 wherein said transducer scanning array is a phased array of transducer elements.

* * * * *